United States Patent [19]
Sanchez-Zambrano

[11] Patent Number: 5,895,414
[45] Date of Patent: Apr. 20, 1999

[54] PACEMAKER HOUSING

[76] Inventor: Sergio Sanchez-Zambrano, Rte. 5, Box 35A, Cleburne, Tex. 76031

[21] Appl. No.: 08/872,200

[22] Filed: Apr. 10, 1997

Related U.S. Application Data

[XX .
[60] Provisional application No. 60/015,844, Apr. 19, 1996.

[51] Int. Cl.$^6$ .................................................. A61N 1/375
[52] U.S. Cl. .................................................. 607/36
[58] Field of Search ................................ 607/36, 9, 37

[56] References Cited

U.S. PATENT DOCUMENTS

| | | |
|---|---|---|
| 3,198,195 | 8/1965 | Chardack . |
| 3,683,933 | 8/1972 | Mansfield . |
| 3,857,398 | 12/1974 | Rubin . |
| 3,971,388 | 7/1976 | Cowdery . |
| 4,256,115 | 3/1981 | Bilitch ........................................ 607/36 |
| 4,301,805 | 11/1981 | Peers-Trevarton et al. . |
| 4,991,582 | 2/1991 | Byers et al. . |
| 5,674,259 | 10/1997 | Gray ........................................ 607/36 |

FOREIGN PATENT DOCUMENTS

| | | |
|---|---|---|
| 2380649 | 9/1978 | France . |
| 3331620A1 | 3/1984 | Germany . |
| WO92/2040 | 11/1992 | WIPO . |

*Primary Examiner*—Scott M. Getzow
*Attorney, Agent, or Firm*—James E. Bradley

[57] ABSTRACT

A pacemaker for providing electrical pulses for a heart has an anatomically-shaped housing. The housing has a concave inner wall and a convex outer wall, which are spaced apart and joined at the periphery. The periphery is elliptical and rounded. The electronics locate within a cavity between the inner and outer walls. An electrical wire extends upward directly above a center of gravity of the housing for connection to the heart. An aperture is located above the center of gravity for suturing to tissue of the patient.

9 Claims, 4 Drawing Sheets

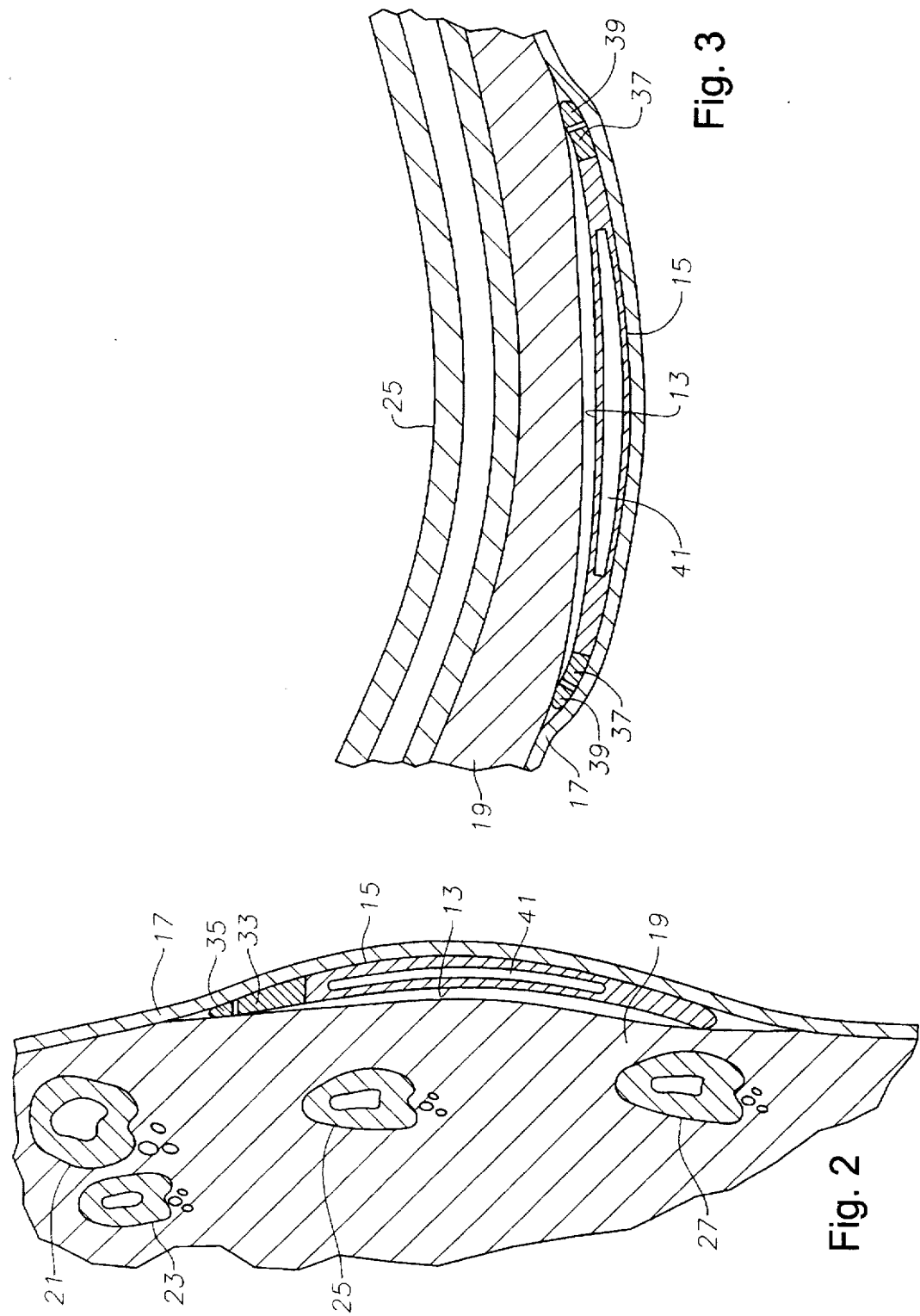

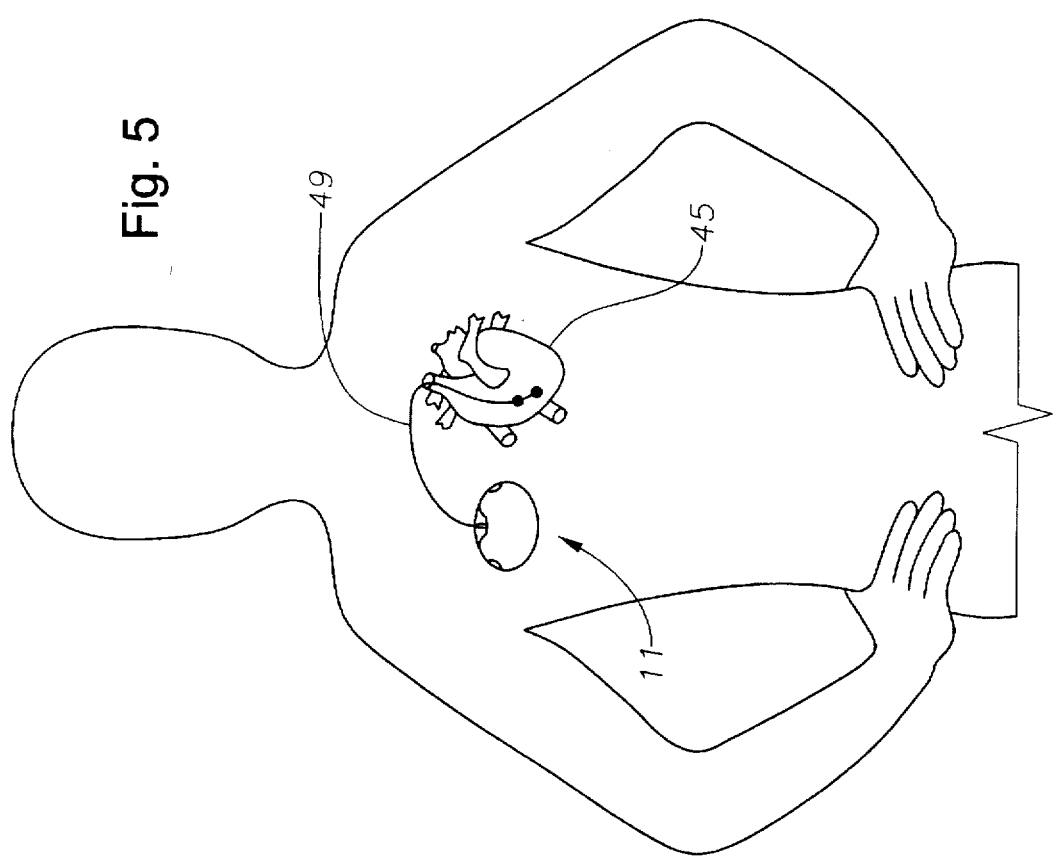
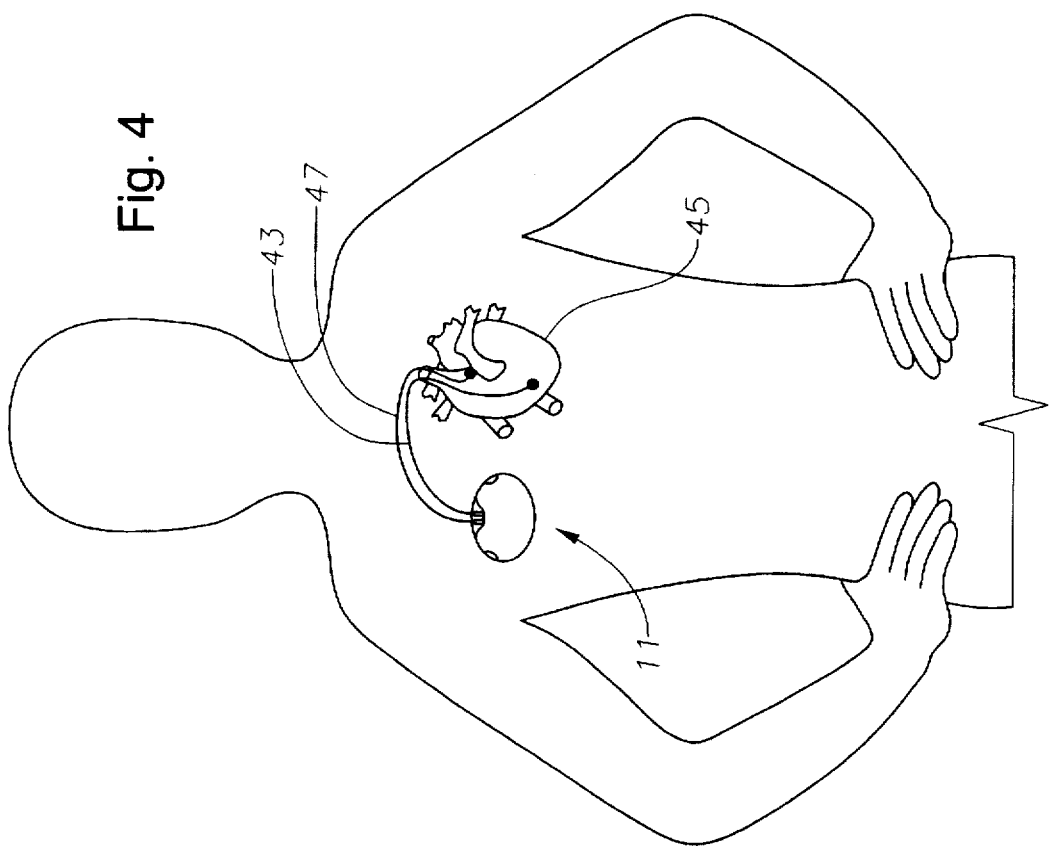

PACEMAKER HOUSING

This application claims benefit of U.S. Provisional application 60/015,844, filed Apr. 19, 1996.

TECHNICAL FIELD

This invention relates in general to pacemakers.

BACKGROUND ART

Pacemakers are primarily implanted into elderly patients more prone to have deteriorated skin tissue. Prior art pacemaker housings are generally rectangular with thicknesses from 3 to 5 millimeters. They are secured to the tissues at a single point and therefore tend to migrate. They are uncomfortable for the patients, produce unsightly bulges, and their exterior edges and corners produce high stress zones on the skin of the patient render it prone to infection.

DISCLOSURE OF INVENTION

The pacemaker of this invention is made with a curved anatomical contour for fitting smoothly under the skin and against the ribcage of the patient. It has a concave inner wall and a convex outer wall, both being at substantially the same angle. The overall configuration is elliptical, with rounded edges.

The electrical leads for connection to the heart protrude upward generally along a vertical line extending upward from the center of gravity. Also, an aperture is located on vertical line located above the center of gravity. A single suture may be employed to stitch the housing in place.

BRIEF DESCRIPTION OF THE DRAWINGS

FIG. 2 is a cross-sectional view of the pacemaker housing of FIG. 1 taken at 2—2 of FIG. 1.

FIG. 3 is a cross-sectional view of the pacemaker housing of FIG. 1 taken at 3—3 of FIG. 1.

FIG. 4 is front elevational view of the dual-chamber embodiment of the pacemaker housing of FIG. 1 shown implanted on the patient's right side.

FIG. 5 is front elevational view of the single-chamber embodiment of the pacemaker housing of FIG. 1 shown implanted on the patient's right side.

BEST MODE FOR CARRYING OUT THE INVENTION

Figure 1:
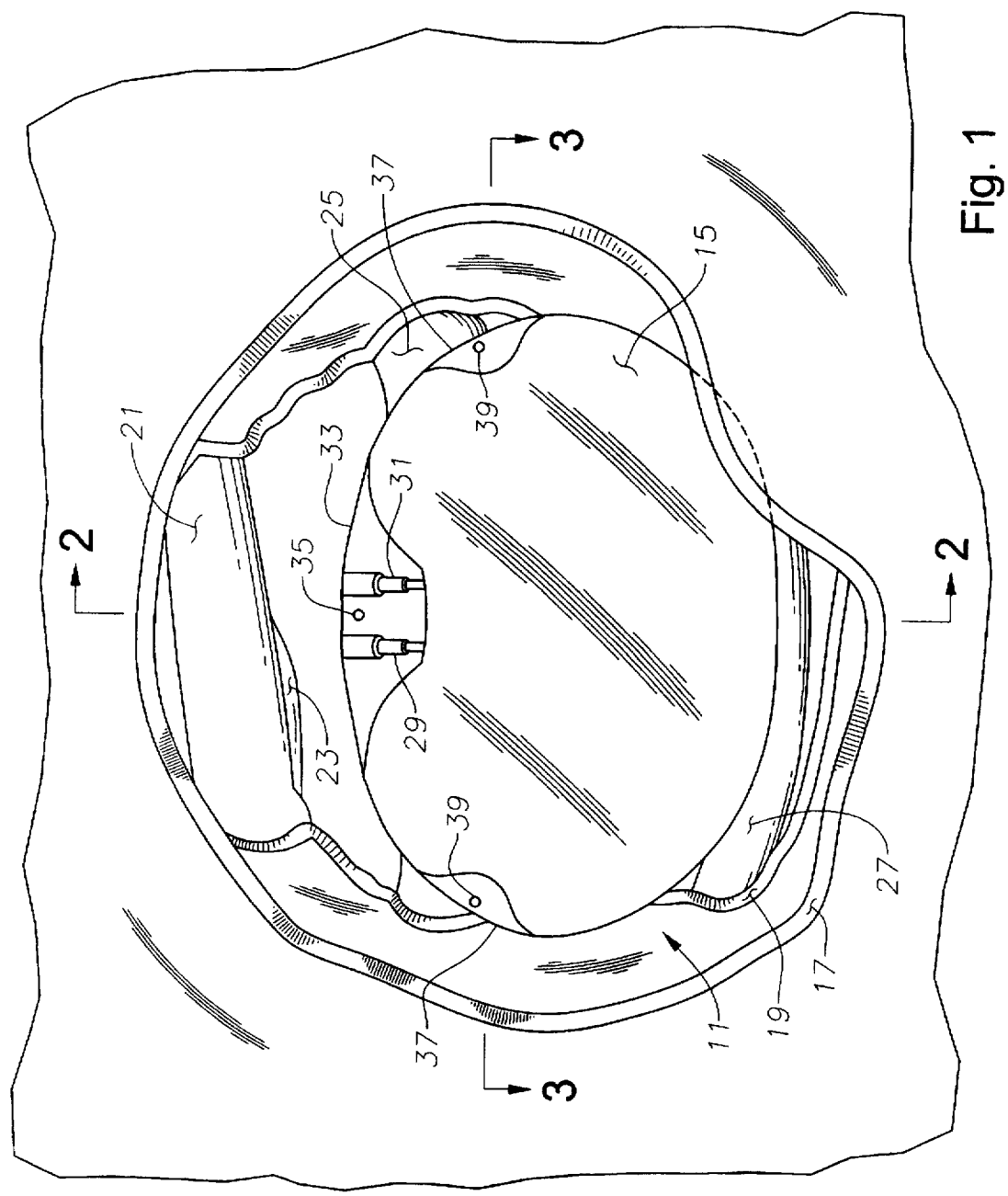
FIG. 1 is a front elevational view of the pacemaker housing of the present invention shown installed in a patient.

Referring to FIGS. 1, 2, and 3, numeral 11 illustrates a concave elliptical pacemaker housing of the present invention with an interior surface 13 and a concentric exterior surface 15. Pacemaker housing 11 has a uniform thickness of 1 to 3 millimeters but tapers smoothly near the periphery to a radius of curvature of 0.4 to 0.6 millimeters. Pacemaker housing 11 is implanted between the patient's skin tissue 17 and muscle tissue 19, below the clavicle bone 21 and third rib 23. Pacemaker housing 11 is secured to the patient's tissue 19. Pacemaker housing 11 contours to the natural curvature of the patient's ribs 25 and 27. Conductive terminals 29, 31 are embedded in, and extend radially upward through a top mounting portion 33, thereby allowing the pacemaker housing 11 to be implanted on either the patient's right or left side, as opposed to currently available units. Separate embodiments of the pacemaker housing 11 have conductive terminals 29, 31 dimensioned to conducively receive either conventional unipolar or bipolar implantable endocardial leads. In the embodiment with a single conductive terminal 29 or 31, the pacemaker housing 11 would house pacemaker electronics for stimulating a single chamber of the heart. In the embodiment with two conductive terminals 29 and 31, the pacemaker housing 11 would house pacemaker electronics for stimulating two chambers of the heart.

Top mounting portion 33 is preferably made of transparent acrylic and contains a mounting means 35 for securing the implanted pacemaker housing 11 to the patient's tissue 19. Top mounting means 35 is located radially above the center of gravity of the pacemaker housing 11, thereby minimizing rotational migration of pacemaker housing 11 when secured utilizing only the top mounting means 35. Top mounting means 35 is preferably an aperture, by which the pacemaker housing 11 is permanently implanted and secured to the patient's tissue 19 with a single suture (not shown) through the patient's tissue 19 and top mounting means 35.

A plurality of side mounting portions 37 are located around the periphery of pacemaker housing 11, and contain side mounting means 39 for securing the implanted pacemaker housing 11 to the patient's muscle tissue 19. Side mounting portions 37 are preferably made of transparent acrylic. Securing the pacemaker housing 11 utilizing two or more side mounting means 39 eliminates rotational migration of pacemaker housing 11. Side mounting means 39 are preferably apertures by which pacemaker housing 11 is permanently implanted and secured to the patient's tissue 19 with single sutures, each through the patient's muscle tissue 19 and a side mounting means 39.

Conventional pacemaker electronics and power source (not shown) are located in the interior cavity 41 of the pacemaker housing 11 and are conducively connected to conductive terminals 29, 31.

Referring now to FIG. 4 in the drawings, pacemaker housing 11, of the dual chamber embodiment, is shown implanted and secured to the patient's tissue 19 on the right side. Conventional implantable unipolar, endocardial lead 43 is conducively received by terminal 31 at one end and fed by conventional surgical methods into endocardial tissue at the opposing end for stimulating the right ventricle of the patient's heart 45. Conventional implantable unipolar, endocardial lead 47 is conducively received by terminal 29 at one end and is fed by conventional surgical methods into endocardial tissue at the opposing end for stimulating the right atrium of the patient's heart 45. Unipolar leads 43 and 47 carry only a positive charge or a negative charge.

Referring now to FIG. 5 in the drawings, pacemaker housing 11, of the single chamber embodiment, is shown implanted and secured to the patient's muscle tissue 19 on the right side. Conventional implantable bipolar, endocardial lead 49 is conducively received by terminal 31 at one end and fed by conventional surgical methods into endocardial tissue at the opposing end for stimulating the right ventricle of the patient's heart 45. Bipolar lead 49 is coaxial and carries both a positive and negative charge.

Figure 6:
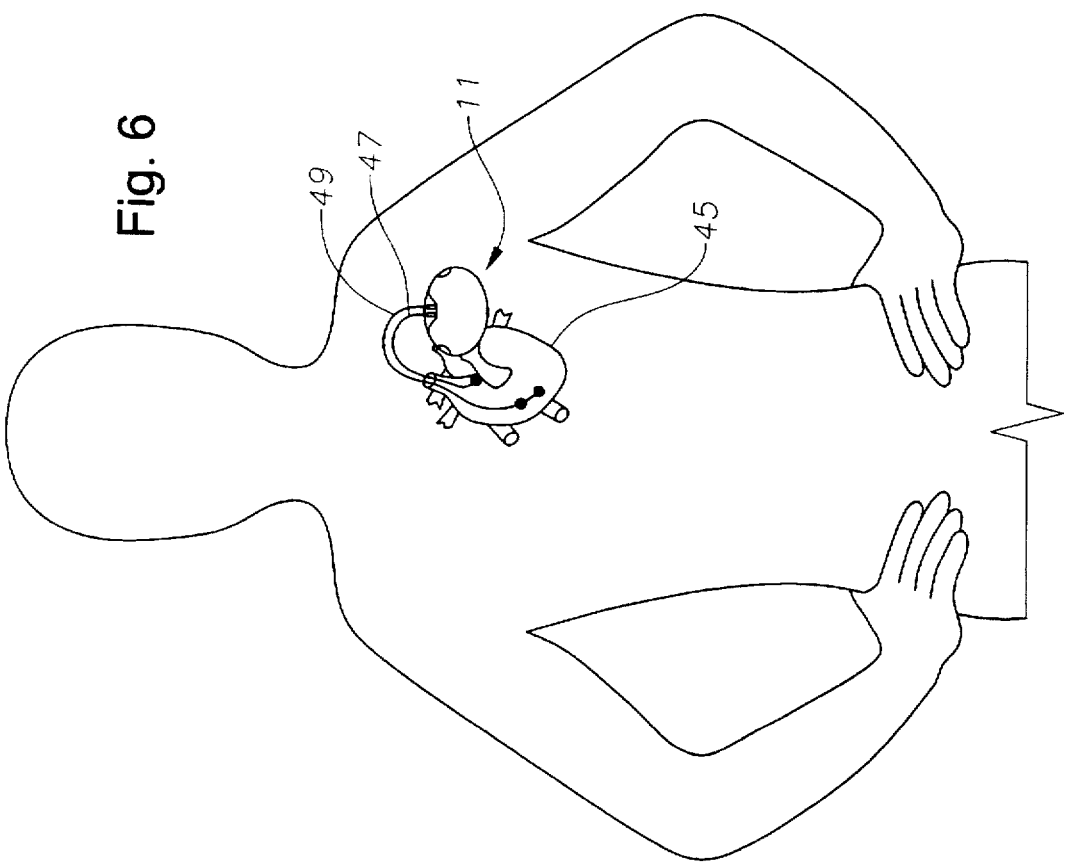
FIG. 6 is front elevational view of the dual-chamber embodiment of the pacemaker housing of FIG. 1 shown implanted on the patient's left side.

Referring now to FIG. 6 in the drawings, pacemaker housing 11, of the dual chamber embodiment, is shown implanted and secured to the patient's muscle tissue 19 on the left side. Conventional implantable bipolar, endocardial lead 49 is conducively received by terminal 31 at one end and fed by conventional surgical methods into endocardial tissue at the opposing end for stimulating the right ventricle of the patient's heart 45. Conventional implantable unipolar, endocardial lead 47 is conducively received by terminal 29 at one end and fed by conventional surgical methods into endocardial tissue at the opposing end for stimulating the right atrium of the patient's heart 45.

Figure 7:
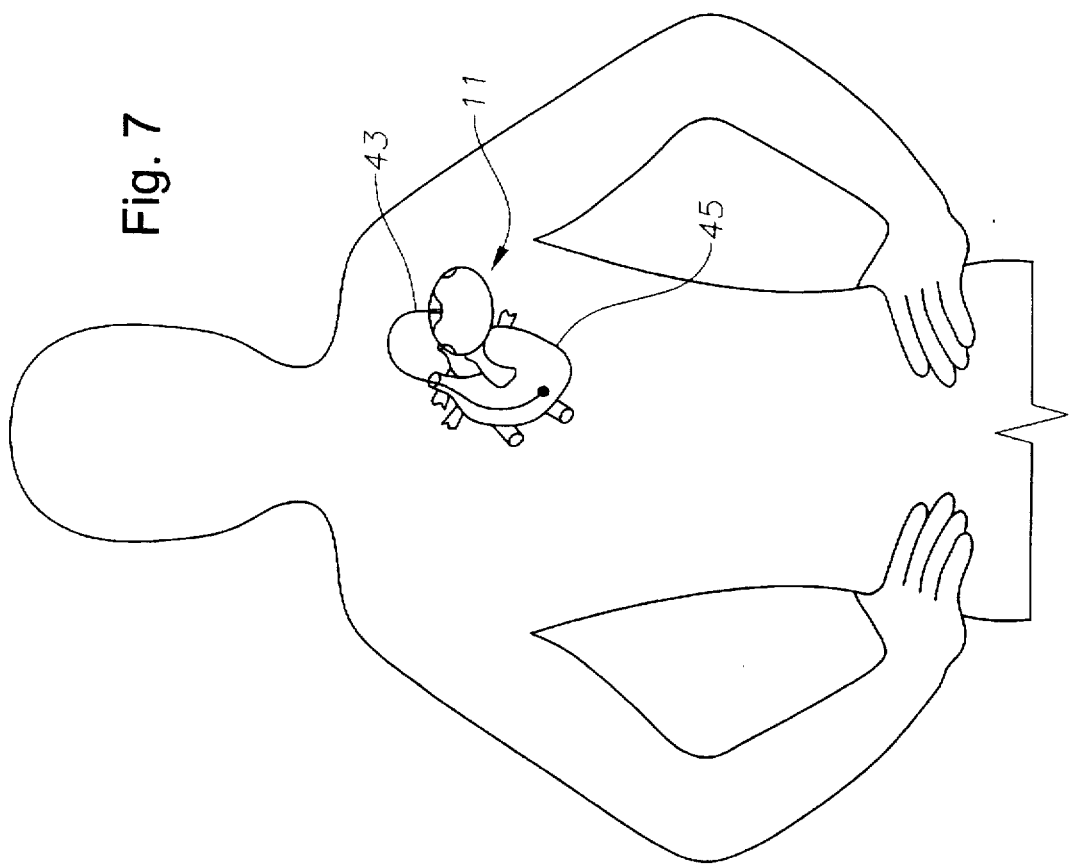
FIG. 7 is front elevational view of the single-chamber embodiment of the pacemaker housing of FIG. 1 shown implanted on the patient's left side.

Referring now to FIG. 7 in the drawings, pacemaker housing 11, of the single chamber embodiment, is shown implanted and secured to the patient's muscle tissue 19 on the left side. Conventional implantable unipolar, endocardial lead 43 is conducively received by terminal 31 at one end and fed by conventional surgical methods into endocardial tissue at the opposing end for stimulating the right ventricle of the patient's heart 45.

It should be apparent from the foregoing that an invention having significant advantages has been provided. The pacemaker housing is anatomically shaped to respect natural curvatures of the bones in a patient's chest. The tapered edges reduce stress on the skin imposed by sharp corners of the prior art types. The placement of the mounting portions reduces migration of the pacemaker. The pacemaker should be lighter in weight over prior art types. The placement of the leads reduces stress to the electrodes and allows the pacemaker to be implanted on both right and left sides.

While the invention is shown in only one of its forms, it is not just limited but is susceptible to various changes and modifications without departing from the spirit thereof.

I claim:

1. A pacemaker for implanting outside of a ribcage of a patient for providing electrical pulses for a heart, comprising:

a housing with a generally concave inner wall having a generally elliptical periphery;

the housing having a generally convex outer wall spaced outward from the inner wall, the outer wall having a generally elliptical periphery which joins the periphery of the inner wall to define a cavity for an electrical circuit;

at least one electrical wire extending from the cavity out an upper edge of the housing for attachment to the heart; and an aperture positioned adjacent the upper edge of the housing for suturing the housing to tissue.

2. The pacemaker according to claim 1 wherein the aperture is positioned on a vertical line extending above a center of gravity of the housing.

3. The pacemaker according to claim 1 wherein the wire extends upward from the housing from a point that is generally vertically above a center of gravity of the housing.

4. A pacemaker for implanting outside of a ribcage of a patient for providing electrical pulses for a heart, comprising:

a housing with a generally concave inner wall having a generally elliptical periphery;

the housing having a generally convex outer wall spaced outward from and generally parallel to the inner wall, the outer wall having a generally elliptical periphery which joins the periphery of the inner wall to define a cavity for an electrical circuit;

at least one electrical wire extending from the cavity out an upper edge of the housing for attachment to the heart; and an aperture positioned adjacent the upper edge of the housing on a vertical line that passes generally through a center of gravity of the housing for suturing the housing to tissue to hold the housing in place.

5. The pacemaker according to claim 4 wherein the wire extends upward from the housing from a point that is generally vertically above a center of gravity of the housing.

6. A method for installing a pacemaker outside of a ribcage of a patient for providing electrical pulses for a heart, comprising:

providing a housing with a generally concave inner wall having a generally elliptical periphery, a generally convex outer wall spaced outward from and generally parallel to the inner wall, the outer wall having a generally elliptical periphery which joins the periphery of the inner wall to define a cavity which contains an electrical circuit, and at least one electrical wire extending from the cavity adjacent the periphery;

providing the housing with at least one aperture positioned adjacent the periphery;

implanting the pacemaker between a patient's skin and ribcage and connecting the wire to the patient's heart; and suturing the housing to tissue of the patient by passing surgical thread through the aperture.

7. The method according to claim 6, wherein the step of providing the housing with at least one aperture comprises placing the aperture adjacent an upper edge of the housing.

8. The method according to claim 6, wherein the step of providing the housing with at least one electrical wire comprises extending the wire from an upper edge of the housing to facilitate placing the pacemaker either on a right side or a left side of the patient.

9. The method according to claim 6, wherein the step of providing the housing with at least one aperture comprises placing the aperture adjacent an upper edge of the housing substantially on a vertical line extending upward from a center of gravity of the pacemaker.

* * * * *